Figure 1A:
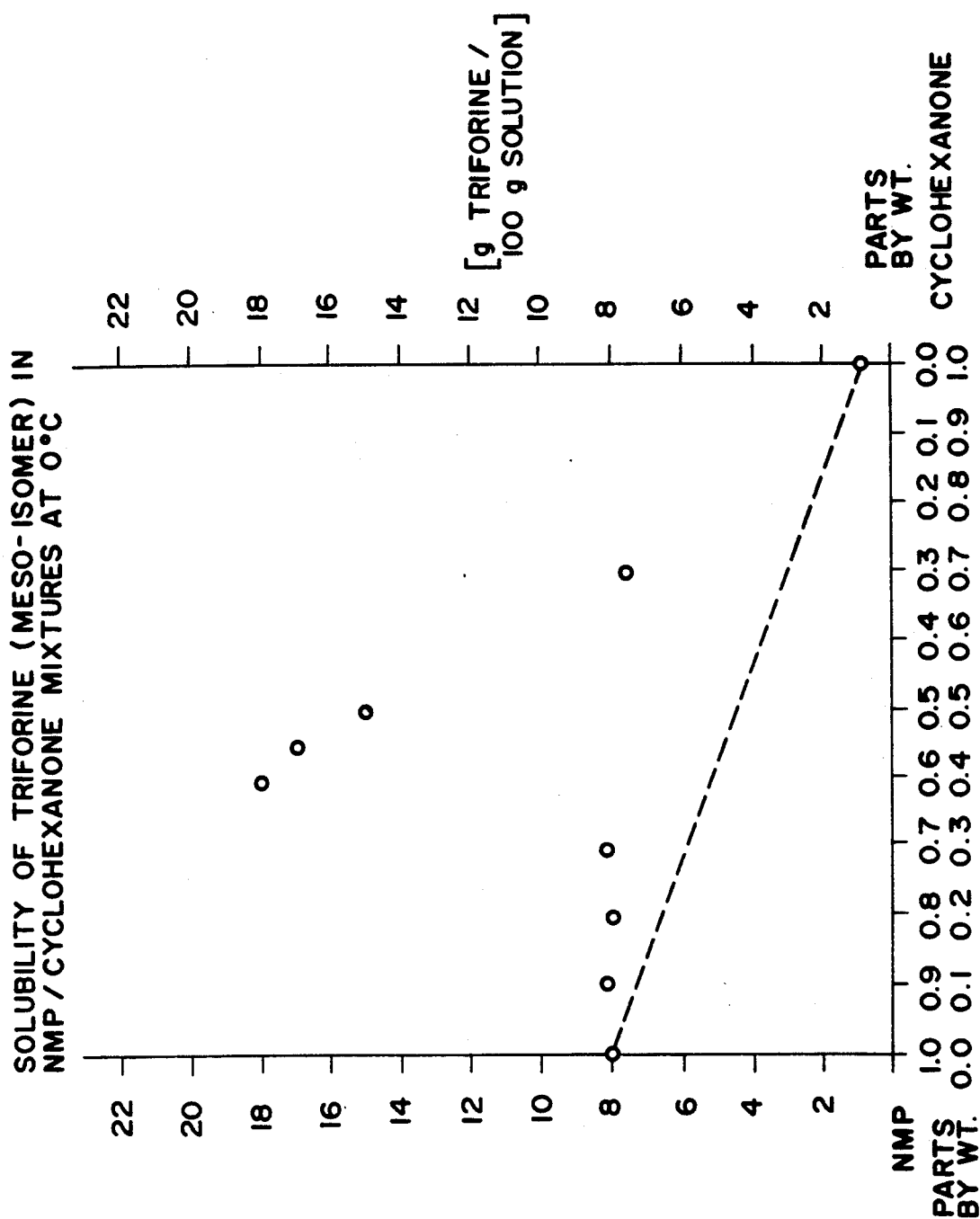
Figure 1B:
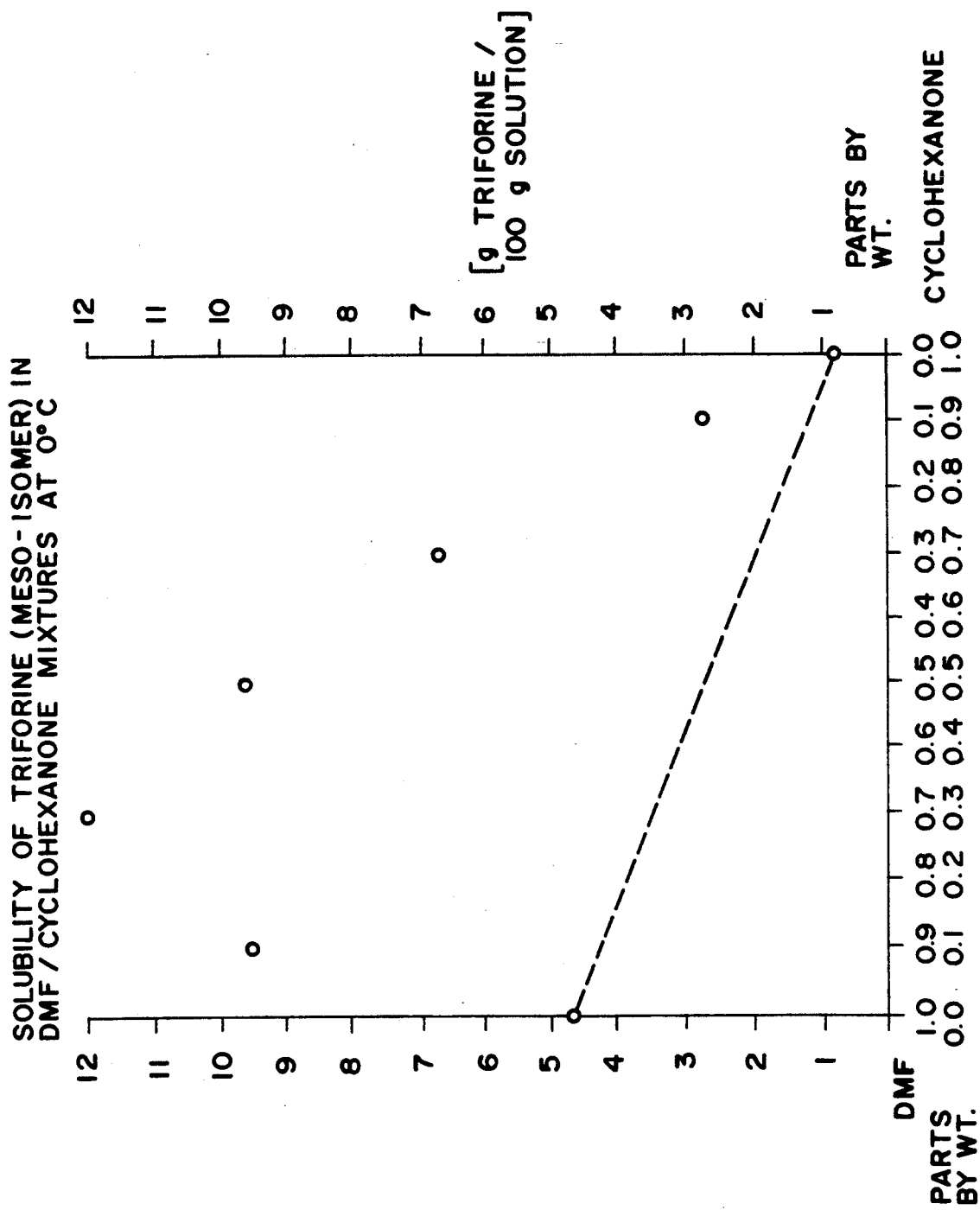
Figure 1C:
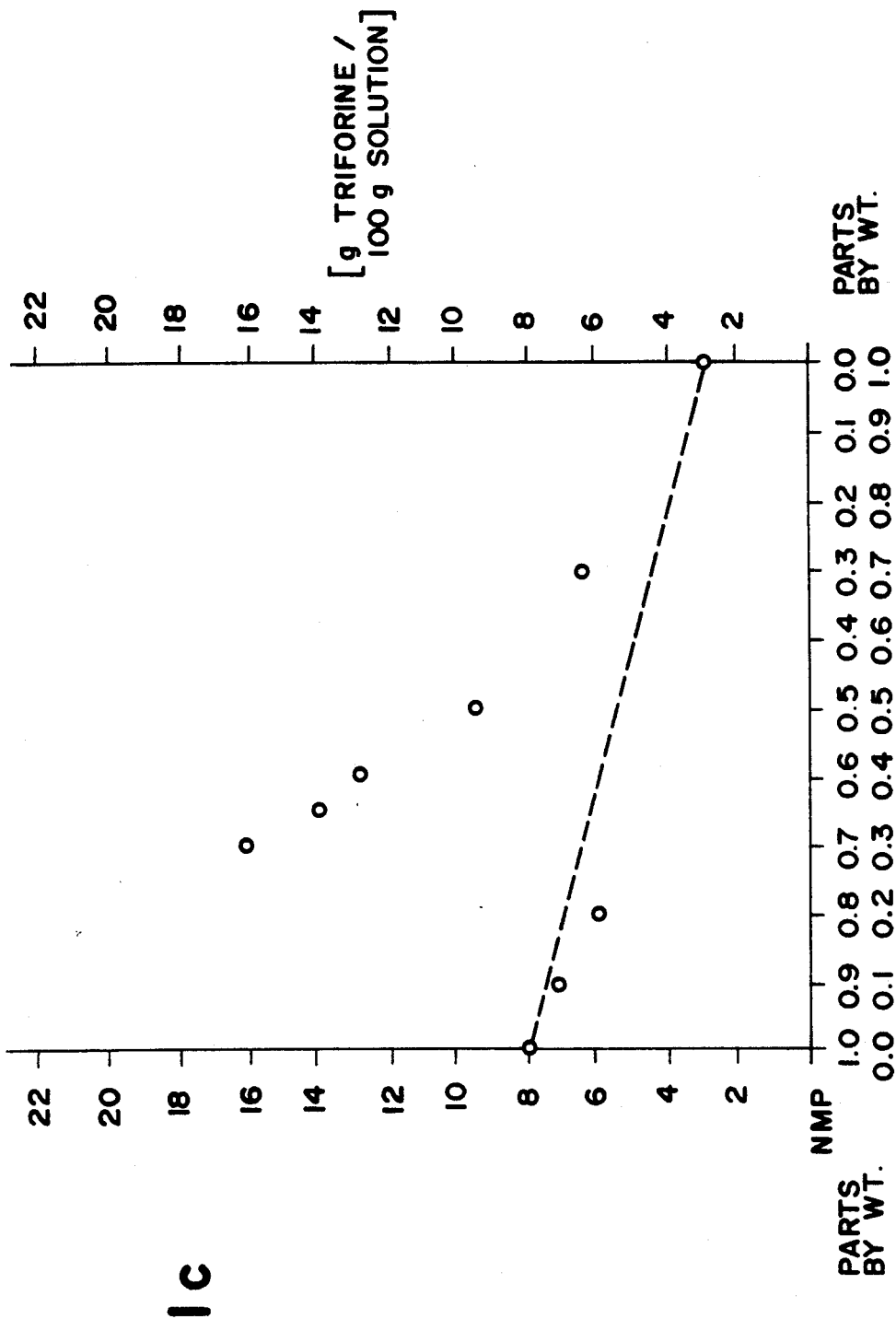

United States Patent [19]

Itzel et al.

[11] Patent Number: 5,141,940
[45] Date of Patent: Aug. 25, 1992

[54] FUNGICIDAL LIQUID FORMULATIONS

[75] Inventors: Hanshelmut Itzel, Weiterstadt; Walter Ost, Bingen am Rhein, both of Fed. Rep. of Germany

[73] Assignee: Shell Internationale Research Maatshappij B.V., The Hague, Netherlands

[21] Appl. No.: 363,263

[22] Filed: May 26, 1989

[51] Int. Cl.$^5$ .......................................... A01N 43/60
[52] U.S. Cl. ................................................. 514/255
[58] Field of Search ................................ 514/184, 255

[56] References Cited

U.S. PATENT DOCUMENTS

| | | | |
|---|---|---|---|
| 3,912,738 | 10/1975 | Ost et al. | 544/400 |
| 3,975,527 | 8/1976 | Ost et al. | 514/255 |
| 4,518,415 | 5/1985 | Marchington et al. | 71/92 |
| 4,521,429 | 6/1985 | Meyer et al. | 514/383 |
| 4,684,396 | 8/1987 | Clough et al. | 7/92 |

FOREIGN PATENT DOCUMENTS 300691 1/1989 European Pat. Off. .

OTHER PUBLICATIONS

CA:111:2696R Detre, Jan. 25, 1989.
Merck index 10th ed. #2720, p. 391.

Primary Examiner—Frederick E. Waddell
Assistant Examiner—Russell Travers

[57] ABSTRACT

The invention provides new solvent concentrates of the fungicidally active substance triforine (N,N'-bis[1-formamido-2,2,2-trichloroethyl]-piperazine) characterized by good solubility and good stability to cold and heat.

2 Claims, 3 Drawing Sheets

FUNGICIDAL LIQUID FORMULATIONS

The invention concerns new solvent concentrates of the fungicidally active substance triforine (N,N-bis[1-formamido-2,2,2-trichloroethyl]-piperazine), which are characterised by high solubility and good stability to cold and heat.

It is known from DE-OS 21 28 225 that a 1:1 mixture of dimethylformamide (DMF) and N-methylpyrrolidone (NMP) has surprisingly good solvent properties for this active substance, which has only poor solubility in the customary organic solvents. Besides the good solubility of the active substance, the low temperature stability in this solvent system is also emphasised. On the other hand, the long-term stability of the solution at storage temperatures above 20° C. is not satisfactory.

Prior art describes solution concentrates of triforine based on DMF/NMP mixtures or with DMF as solvent, for which the long-term stability of the solutions has been decidedly improved by means of new emulsifiers at storage temperatures up to 30° C.

Furthermore, it is known from DE-OS 23 06 623 that the substance triforine can be separated into two isomeric compounds and that the different solubility of the isomers in various solvents can be utilised.

It is apparent therefore that the long-term stability of the active substance concentrate hitherto achieved is not always adequate for the conditions which occur in practice. A satisfactory storage stability up to 30° C. can be achieved with the solution concentrates described in DE-OS 25 20 048. However, plant protectants are often also exposed to higher temperatures for long periods. The temperature limit of 30° C. is frequently exceeded during storage under glass (e.g. greenhouses, windows) or in buildings which are directly exposed to sunlight (e.g. store sheds) or in Mediterranean or tropical zones. The result of this is that there is severe decomposition of the active substance of the solvent concentrates.

The search for new stable concentrates for the plant protectant triforine is made more difficult in particular by the fact that triforine has poor solubility in many organic solvents.

It has now been found, surprisingly, that mixtures of DMF or NMP with cyclohexanone and/or 2-hydroxymethyltetrahydrofuran (tetrahydrofurfuryl alcohol, THF-ol) and/or dimethylsulphoxide (DMSO) have very good solvent properties for triforine, with the mixtures having better solvent powers than the best pure solvent of each mixture by a factor of 2 to 3.8. Besides the unexpected synergistic solvent action, the solvent mixtures according to the invention have very good low temperature stability and also high storage stability at temperatures above 30° C.

The combined results of the solubility test given in Example 1 illustrate the surprising synergistic solvation effect of the mixtures according to the invention.

The tests were carried out on the less soluble meso-isomer of triforine. When using triforine of technical purity, which is a mixture of all three stereoisomeric compounds, the solubility can clearly be increased still further.

The improved solubility of triforine is advantageously found in NMP/cyclohexanone, DMF/cyclohexanone, DMF/DMSO, NMP/DMSO, NMP/cyclohexanone/THF-ol or DMF/cyclohexanone/THF-ol systems containing NMP or DMF respectively in the range of 0.3 to 0.9 parts by weight. The range is preferably 0.5 to 0.8 parts by weight NMP or DMF respectively.

The solvent effect of the binary systems NMP/cyclohexanone or DMF/cyclohexanone can be increased by adding THF-ol. In the NMP-THF-ol system, triforine has particularly good solubility in mixtures with 0.5 to 0.75 parts by weight NMP. The solvent effect of the binary system NMP/THF-ol can be further increased by adding cyclohexanone.

The term "parts by weight" is used in accordance with the definition normally used in technical chemistry (Lit.: P. Grassman and F. Widmer; Einführung in die thermische Verfahrenstechnik; 2nd edition, Berlin, 1974 pp. 10, 11).

As formulation examples 2a to 2g show, concentrates of the active substance with a content of technically pure triforine of 15 to 25% can be produced by mixing with the solvents according to the invention. These formulations have good low temperature stability and even when stored for several months at 0° C. show no changes in their physical properties. However, because of the good solvent properties of the solvent mixtures according to the invention, it is also possible to produce solution concentrates with a triforine content of over 25%.

The clearly improved storage stability at higher temperatures should be emphasised in particular. As the results of Example 3 show, decomposition of the active substance is less than 2.5% even after 6 months' storage.

EXAMPLES

1. Synergistic solvent action

Because of the difficulties involved in obtaining accurate data on the solubility of the substance triforine, which consists of three optical isomers, tests were only carried out on the meso-isomer which has the poorest solubility.

The solubility of technically pure triforine is given as a control in the case of some mixtures. Solubility is determined at 0° C. The mixture ratios and solubilities are given in ratios of weight.

TABLE 1

| Solvent system | Ratio | g/100 g solution meso form | technical triforine |
| --- | --- | --- | --- |
| DMF (Dimethylformamide) | | 4.7 | — |
| NMP (N-methylpyrrolidone) | | ca. 8.0 | — |
| DMSO (Dimethylsulphoxide) | | 1.0 | — |
| Tetrahydrofurfurylalcohol (THF-ol) | | 3.0 | — |
| Cyclohexanone | | 0.8 | — |
| NMP/Cyclohexanone | 3:7 | 7.6 | 13.8 |
| NMP/Cyclohexanone | 5:5 | 15.0 | 20.0 |
| NMP/Cyclohexanone | 5.5:4.5 | 17.0 | — |
| NMP/Cyclohexanone | 6:4 | 18.0 | — |
| NMP/Cyclohexanone | 7:3 | 8.2 | — |
| NMP/Cyclohexanone | 8:2 | 8.0 | — |
| NMP/Cyclohexanone | 9:1 | 8.1 | — |
| NMP/Cyclohexanone/THF-ol | 1:1:1 | 8.8 | — |
| NMP/Cyclohexanone/THF-ol | 4.5:4.5:1 | 12.1 | — |
| NMP/Cyclohexanone/THF-ol | 6:2:2 | 14.5 | — |
| NMP/Cyclohexanone/THF-ol | 7:3:1 | 17.5 | — |
| NMP/Cyclohexanone/THF-ol | 7:2:1 | 19.0 | 25.5 |
| NMP/Cyclohexanone/ | 8:1:1 | 6.6 | — |

TABLE 1-continued

| Solvent system | Ratio | g/100 g solution meso form | technical triforine |
|---|---|---|---|
| THF-ol | | | |
| NMP/THF-ol | 9:1 | 7.2 | — |
| NMP/THF-ol | 8:2 | 6.2 | — |
| NMP/THF-ol | 7:3 | 16.1 | — |
| NMP/THF-ol | 6.5:3.5 | 14.1 | — |
| NMP/THF-ol | 6:4 | 12.8 | — |
| NMP/THF-ol | 5:5 | 9.2 | — |
| NMP/THF-ol | 3:7 | 6.6 | — |
| DMF/Cyclohexanone/THF-ol | 1:1:1 | 8.0 | — |
| DMF/Cyclohexanone/THF-ol | 7:3:1 | 10.1 | — |
| DMF/Cyclohexanone/THF-ol | 7:2:1 | 10.9 | — |
| DMF/Cyclohexanone/THF-ol | 8:1:1 | 7.0 | — |
| DMF/Cyclohexanone | 1:9 | 2.7 | — |
| DMF/Cyclohexanone | 3:7 | 6.7 | — |
| DMF/Cyclohexanone | 1:1 | 9.6 | — |
| DMF/Cyclohexanone | 7:3 | 12.0 | — |
| DMF/Cyclohexanone | 9:1 | 9.5 | — |
| NMP/DMSO | 1:1 | 24.0 | 30.0 |
| DMF/DMSO | 1:1 | 18.0 | — |

2. Formulation examples

Technical triforine (i.e. mixture of the three stereoisomers) is used for the formulation examples. The triethylamine salt of dodecylbenzenesulphonic acid (DBS salt) is used as emulsifier. The quantities given in weight ratios (% w/w).

| | % w/w |
|---|---|
| 2a. NMP/Cyclohexanone/THF-ol 7:2:1 | |
| Triforine | 18.9 |
| DBS-salt (Emulsifier) | 25.0 |
| Polyvinylacetate/Polyvinylpyrrolidone-copolymer (Stabilizer) | 2.0 |
| THF-Alcohol | 5.3 |
| Cyclohexanone | 10.6 |
| NMP ad 100 | 38.2 |
| 2b. NMP/Cyclohexanone 6.2:3.8 | |
| Triforine | 19.0 |
| DBS-salt (Emulsifier) | 16.0 |
| Isotridecylalcoholpolyglycolether (Emulsifier) | 7.5 |
| Cyclohexanone | 22.0 |
| NMP ad 100 | 35.5 |
| 2c. DMF/Cyclohexanone 6.4:3.6 | |
| Triforine | 15.0 |
| DBS-salt (Emulsifier) | 16.0 |
| Isotridecylalcoholpolyglycolether (Emulsifier) | 7.5 |
| Cyclohexanone | 22.0 |
| DMF ad 100 | 39.5 |
| 2d. NMP/THF-ol 7:3 | |
| Triforine | 20.0 |
| DBS-salt (Emulsifier) | 25.0 |
| THF-ol | 16.5 |
| NMP ad 100 | 38.5 |
| 2e. NMP/Cyclohexanone/THF-ol 6.7:2.2:1.1 | |
| Triforine | 15.0 |
| DBS-salt (Emulsifier) | 10.0 |
| Isotridecylalcoholpolyglycolether (Emulsifier) | 7.5 |
| THF-ol | 7.5 |
| Cyclohexanone | 15.0 |
| NMP ad 100 | 45.0 |
| 2f. DMSO/NMP 1:1 | |
| Triforine | 25.0 |
| DBS-salt (Emulsifier) | 25.0 |
| DMSO | 25.0 |
| NMP ad 100 | 25.0 |
| 2g. DMSO/DMF 4.5:5.5 | |
| Triforine | 20.0 |
| DBS-Salt (Emulsifier) | 25.0 |
| DMSO | 25.0 |
| DMF ad 100 | 30.0 |

The solution concentrates described are stable during storage and show no change in their physical properties even when stored for several months at 0° C.

3. Storage stability

In order to determine storage stability, samples of the concentrates according to the invention were stored for 6 months at 37° C., after which the relative decomposition was determined in % in relation to the initial quantity of active substance.

| Example 7 | from DE 21 28 225 | 20% |
|---|---|---|
| Example 2a | (according to the invention) | less than 2.5% |
| Example 2b | " | " 2.5% |
| Example 2c | " | " 2.5% |

We claim:

1. A liquid formulation of N,N'-bis(1-formamido-2,2,2-trichloroethyl)piperazine, characterized in that it contains as solvent a mixture of 0.5 to 0.38 parts by weight cyclohexanone and 0.5 to 0.62 parts by weight N-methylpyrrolid-2-one.

2. A liquid formulation of N,N'-bis(1-formamido-2,2,2-trichloroethyl)piperazine, characterized in that it contains as solvent a mixture of 0.7 to 0.1 parts by weight cyclohexanone and 0.3 to 0.9 parts by weight dimethylformamide.

* * * * *